United States Patent [19]

Zimmerman

[11] Patent Number: 5,130,491

[45] Date of Patent: Jul. 14, 1992

[54] CONTINUOUS PREPARATION OF SECONDARY AMINES FROM NITRILES USING A NICKEL CATALYST

[75] Inventor: Robert L. Zimmerman, Austin, Tex.

[73] Assignee: Texaco Chemical Company, White Plains, N.Y.

[21] Appl. No.: 583,110

[22] Filed: Sep. 17, 1990

[51] Int. Cl.⁵ .......................................... C07C 209/00
[52] U.S. Cl. .................................. 564/490; 564/470; 564/493
[58] Field of Search ................ 564/470, 490, 493; 502/301, 315

[56] References Cited

U.S. PATENT DOCUMENTS

| | | | |
|---|---|---|---|
| 2,781,399 | 2/1957 | Shapiro | 260/583 |
| 2,811,556 | 10/1957 | Shapiro | 260/583 |
| 3,733,325 | 5/1973 | Yeakey | 544/402 |
| 4,248,801 | 2/1981 | Tomidokoro et al. | 564/463 |

FOREIGN PATENT DOCUMENTS

| | | |
|---|---|---|
| 0021162 | 1/1981 | European Pat. Off. |
| 0232097 | 8/1987 | European Pat. Off. |
| 0133229 | 12/1978 | German Democratic Rep. |
| 0759291 | 10/1956 | United Kingdom. |
| 1180972 | 2/1970 | United Kingdom. |
| 1323351 | 7/1973 | United Kingdom. |

OTHER PUBLICATIONS

Tomidokoro, S., et al., "Preparation of Long-Chain Secondary Amines by Reduction of Nitriles," *Chemical Abstracts*, 106:175777t, Japan Tokkyo Koho JP 62 00,901; 1987, p. 671.

*Primary Examiner*—Allen J. Robinson
*Assistant Examiner*—Peter G. O'Sullivan
*Attorney, Agent, or Firm*—Jack H. Park; Kenneth R. Priem; David L. Mossman

[57] ABSTRACT

A method for producing secondary amines, particularly fatty secondary amines such as ditallowamine from fatty nitriles, such as tallow nitrile over a nickel catalyst promoted with copper, chromium and molybdenum has been discovered. The reaction gives high selectivity of secondary amine over the coproduced primary and tertiary amines. The reaction may be conducted continuously in the presence of ammonia and hydrogen. The secondary amine proportion may be increased by a second stage using the same catalyst as the first stage, but in the absence of ammonia. The same catalyst may be used in both steps if a two stage process is used.

9 Claims, No Drawings

CONTINUOUS PREPARATION OF SECONDARY AMINES FROM NITRILES USING A NICKEL CATALYST

CROSS-REFERENCE TO RELATED APPLICATION

The present application is related to U.S. patent application Ser. No. 07/506,747 filed Apr. 10, 1990 now U.S. Pat. No. 5,075,506, relating to the continuous preparation of secondary amines from nitriles using cobalt catalysts promoted with zirconium.

FIELD OF THE INVENTION

The invention relates to the production of secondary amines from nitriles, and, in one aspect, more particularly relates to the continuous production of secondary amines from nitriles using a single transition metal catalyst, in particular, a nickel catalyst.

BACKGROUND OF THE INVENTION

It has long been known that nitriles can be reduced to give amines. Typically a mixture of primary, secondary and tertiary amine are produced, and a common goal is to devise a process by which the result is a yield high in only one of the possible products; that its, has high selectivity to a particular product. The reaction is understood to proceed in two steps, and often the process is a two step process, usually using a different catalyst for the two steps. Frequently, the reaction is run as a bach reaction inasmuch as good selectivities have been difficult to achieve using continuous processes.

Particularly useful products from the reaction are the secondary amines. They have found such widespread uses as textile additives, disinfectants, antistatic agents, and organophoilic ammonium bentonites. Especially useful are the unsaturated long-chain aliphatic secondary amines since the quaternary ammonium salts thereof can provide softness and antistaticity to various fabrics and hair , and can also be used as a softener for providing water absorbancy and handling ease to treated fabrics. The secondary amine ditallowamine is useful in the preparation of surfactants, but has never been continuously prepared in high selectivity from tallow nitrile. Tallow nitrile has sixteen to eighteen carbon atoms ($C_{16}$ to $C_{18}$).

Of particular interest is British Patent 1,180,972 (equalivant to Oberrauch, Hans, et al. "Secondary Fatty Amines," *Chemical Abstracts,* 70:11108n, West German Patent 1,280,243, 1969, p. 221) which teaches that aliphatic, saturated and unsaturated secondary fatty amines can be prepared by hydrogenation of the corresponding fatty acid nitrile by passing the nitrile at 140–200° C. and 30–200 atm. of hydrogen together with water over a solid catalyst consisting of 20% copper, 0.8% chromium and 1% alkali metal with a wide-poured silica gel having a specific area of 250–350 m.$^3$/g as the support. See also British Patent 1,323,351 (equivalent to West German Auslegeschrift 1,941,290) which describes a process of making aliphatic saturated secondary amines from nitriles having 8 to 22 carbon atoms per molecule, where in a first step the starting product is hydrogenated to yield a mixture of saturated amines, and in a second step, this mixture is continuously desaminated (i.e., ammonia is split off) optionally with the addition of hydrogen, where each step is carried out in the presence of a fixed bed hydrogenation catalyst. The first step is conducted at a hydrogen pressure of from 100 to 300 atmospheres gauge and at a temperature in the range of from 100 to 200° C., while the second step is conducted at a pressure from 0 to 50 atmospheres and at a temperature in the range from 120 to 220° C. The catalysts used are a cobalt catalyst in the first step and then a copper catalyst; or alternatively a nickel catalyst in the first reaction and a cobalt catalyst in the second.

Tertiary monomethylamines having long chain alkyl groups are advantageously prepared form unsaturated aliphatic nitriles under a low pressure at a high yield by a three strep process according to U.S. Pat. No. 4,248,801. The first step involves reducing nitriles with hydrogen in the pressure of 0 through 10 kg/cm$^2$G, while the formed ammonia is removed.

Of lesser importance is the following group of publications, which includes U.S. Pat. No. 2,781,399, (equivalent to British Pat. 759,291) that teaches production of secondary aliphatic hydrocarbon amines via a batch reaction using a nickel hydrogenation catalyst. A similar process is presence of a nickel hydrogenation catalyst of 200° C. and under a hydrogen described in U.S. Pat. No. 2,811,556, except that a copper oxide/chromium oxide catalyst is used.

Tomidokoro, S., et al., "Preparation of Long-Chain Secondary Amines by Reduction of Nitriles," *Chemical Abstracts,* 106:175777t, Japan Tokkyo Koho JP 62 00.901, 1987, p. 671, teaches the preparation of long-chain secondary amine by the reduction of aliphatic nitrile having 8 to 22 carbon atoms over nickel catalysts at 0–6 kg/cm$^2$ gauge and 200 to 230° C. while removing more than 85% formed $NH_3$. Thus, 250 g. of tallow nitrile was reduced over 0.5 g. Nicatalyst at 200–300° C. and 5 kg/cm$^2$ while removing 93% formed $NH_3$ to give 240 g. of a mixture of primary (3.1%), secondary (91.1%) and tertiary amine (4.3%) amines.

European patent 0 021 162 B1 teaches the production of alkylamines with 12 to 22 carbon atoms by hydrogenating corresponding fatty nitriles in the presence of a nickel or cobalt catalyst. The hydrogen gas reactant is recirculated after removal of ammonia. The new feature is that throughout the reaction the water content of the circulating gas is adjusted to not above 5 g. per cubic meter, under practically zero-pressure conditions, before recycle. Additionally, a process for selectively preparing an unsaturated long-chain aliphatic secondary amine at a high yield involving reducing an unsaturated aliphatic nitrile having 8 to 322 carbon atoms or a nitrile mixture containing said nitrile with hydrogen in the presence of nickel hydrogenation catalyst and a carboxylic acid amide at a reaction temperature of 160 to 200° C. is described in European Patent Application 0232097 A2.

A process for the selective production of aliphatic secondary amines from $C_{3-22}$ primary amines using dehydrogration/hydrogenation catalysts is briefly mentioned in the English abstract to East German Application 133,229-A. In a first stage, the primary amine is dehydrogenated at normal pressure and at 1760 to 260° C., by treatment with a inert gas ($N_2$) in an amount of 5 to 150 l/mol./h., for 30 to 60 minute until a degree of conversion of the starting material of 85-98% is achieved. The resulting dehydrogenated product is then reacted with hydrogen at 100 to 140° C. and 0 to 50 atmospheres for 10 to 30 minutes to form the secondary amine. The nature of the catalyst was not mentioned in the abstract.

There remains a need for a continuous process for producing fatty secondary amines simply, and in high selectivities. Ideally, such a process would only use one catalyst.

SUMMARY OF THE INVENTION

Accordingly, it is an object of the present invention to provide a process for the continuous production of fatty secondary amines.

It is another object of the present invention to provide a continuous process for making fatty secondary amines that requires only one catalyst.

Another object of the invention is to provide a continuous process for producing fatty secondary amines in high selectivity.

In carrying out these and other objects of the invention, there is provided, in one form, a continuous process for the preparation of secondary amines from nitriles comprising continuously passing a nitrile over a nickel catalyst promoted with effective amounts of copper, chromium and molybdenum.

DETAILED DESCRIPTION OF THE INVENTION

It has been discovered that secondary amines, particularly fatty secondary amines such as ditallowamine may be produced in high selectivity by passing corresponding nitrile, such as tallow nitrile, over a nickel catalyst promoted with effective amounts of copper, chromium and molybdenum.

The invention is particularly suited for producing fatty secondary amines from fatty nitriles, which are defined as having from about 8 to about 22 carbon atoms. A preferred feedstock because of its relative inexpensiveness is tallow nitrile which has from about 16 to 18 carbon atoms. The product from this feedstock is ditallowamine, also known as di(hydrogenated tallow)amine. Of course, the resulting secondary amine has twice the carbon atoms of the beginning nitrile.

As noted, the catalyst should be a nickel hydrogenation-dehydrogenation catalyst, such as nickel oxide. Another suitable nickel catalyst is nickel metal, but the process is not limited to these two nickel materials. Preferably, the promoters are copper, chromium and molybdenum in forms such as copper oxide, chromium oxide and molybdenum oxide, for example. In one aspect, the nickel proportion of the catalyst should range from about 30 to about 70%, preferably from about 40 to about 60%. The promoters, such as copper, chromium and molybdenum in oxide form, should be present in an amount great enough to give a promotive effect. In one aspect, the amount of promoter may range from about 2 to about 18%, more preferably from about 5 to about 12%. In one embodiment, the metal composition is present in about a 50 wt. % proportion, and in another embodiment, the metal compositions are supported, such as on alumina.

The reaction is preferably conducted at elevated temperatures and pressures. For example, the temperature may range from about 100 to about 200° C., preferably from about 130 to about 180° C. The pressure may range from about 50 to about 5000 psig, and more preferably range from about 200 to about 1000 psig. It is preferred a that ammonia and hydrogen are present during the reaction. A solvent, such as cyclohexne for example only, may optionally be employed in the reaction. Other suitable inert solvents may include, but are not limited to, straight, branched and cyclic alkanes having up to about twelve carbon atoms.

The reaction may be conducted in one or two steps. It has also been surprisingly discovered if the reaction is conducted in two continuous stages that ammonia is preferably not present in the second stage; whether using the catalyst of this invention, a cobalt catalyst, or other hydrogenation-dehydrogenation catalyst, the absence of ammonia in the second step is preferred since primary amines are formed in the first reaction, and the production of the secondary amines from two primary amines in the second step also produces an ammonia molecule. Thus, the absence of ammonia in the second step would facilitate the second reaction. Surprisingly, it was also discovered that the same catalyst maybe used even if a two-step process is desired. As will be shown, the inventive process using the Ni-Cu-Cr-Mo catalyst gives a higher secondary amine content than other known processes.

The use of a continuous reaction has advantages over the batch reactions in that no filtration or loss of catalyst is experienced, since a fixed bed is used in the continuous reaction. The invention will be illustrated in greater detail with reference to the following examples. All analyses were performed by wet chemistry (titration) in a manner similar to, if not identical to, ASTM methods for determining tallow amines.

EXAMPLE 1

Production of Ditallowamine Using Ni-Cu-Cr-Mo Catalyst

For the following experiments a tubular reactor filled with 600 cc of catalyst was used. The catalyst used was a Ni-Cu-Cr-Mo catalyst. Tallow nitrile was fed into the continuous reactor at a rate of 0.28 lb/hr., cyclohexane was fed at 0.57 lb/hr., ammonia at 0.06 lb/hr. and hydrogen at 387 l/hr. The reactor pressure was 500 psig and the hot spot temperature was about 155° C. The ammonia and cyclohexane were removed from the crude produce under reduced pressure. This crude product contained about 50.5% primary amine, 48.6% secondary amine and 0.9% tertiary amine. This crude product was then passed through the reactor again along with cyclohexane ad hydrogen. The rates were 0.36 lb/hr hydrogenated crude product, 0.72 lb/hr cyclohexane and 355 l/hr hydrogen. No ammonia was fed on the secondary pass. The hot spot temperature was about 160° C. and the pressure was 500 psig. The product was stripped under vacuum. The analysis on the finished product showed 4.5% primary amine, 93.2% secondary amine (ditallowamine) and 2.3% tertiary amine.

The yield of secondary amine (hydrogenated ditallowamine) is better than 90.3% in example 1 of British Patent 1,323,351, or the 90.5% in example 1 of British Patent 1,180,972.

COMPARATIVE EXAMPLE 2

Production of Ditallowamine Using Ni-Cu-Cr Catalyst

The reactor of Example 1 was used in this Example, but the catalyst used was a conventional Ni-Cu-Cr catalyst. The feed rates for the first pass were tallow nitrile at 0.28 lb/hr., cyclohexane 0.57 at lb/hr., ammonia at 0.06 lb/hr. and hydrogen at 387 l/hr. The hot spot temperature was 140° C. and the pressure was 500 psig. The crude product had the following analysis: 44.6% primary amine, 53.6% secondary amine and 1.9% tertiary amine. The crude product was placed through the reactor again with the feed rates being: crude product at 0.36 lb/hr., cyclohexane at 0.73 lb/hr. and hydrogen at 387 l/hr. As in Example 1, no ammonia was used on the second pass. The hot spot temperature was about 185° C. and the pressure was 500 psig. The product was stripped under vacuum. Analysis of the final product was: 11.3% primary amine, 83.0% secondary amine and 5.7% tertiary amine. It can be seen that the yield and selectively to secondary amine in Example 2 using a conventional catalyst is not as great as that of Example 1 using the inventive catalyst.

Thus, better yields of hydrogenated ditallowamine are achieved using the catalyst of this invention than in prior art continuous processes using Ni-Cu-Cr catalysts. No filtration or catalyst loss problems occur in this continuous process, as in the batch process. Another unexpected advantage of the process is that only one catalyst is used, rather than two, as in the prior art processes. As noted, using two passes through the same reactor with the same catalyst, only not using ammonia with the second pass has also aided in increasing the selectivity to the second amine using transition metal catalysts, such as the nickel catalyst described above and a cobalt catalyst promoted with zirconium, described in more detail in U.S. patent application Ser. No. 07/506,747 incorporated by reference herein. Examples of this two pass, continuous process giving higher secondary amine content as compared with a single pass are given below.

EXAMPLE 3

Single Pass Using a Ni-Cu-Cr-Mo Catalyst

A tubular reactor filled with 600 cc of catalyst was used for the reaction. The catalyst was the nickel-copper-chromium-molybdenum catalyst used in Example 1. The pressure was 500 psia and the hydrogen feed rate was 387 l/hr.. The products resulting at various reaction temperatures are given in Table V.

EXAMPLE 4

Double Pass Using a Ni-Cu-Cr-Mo Catalyst

The same reactor, catalyst, hydrogen feed and pressure were for this Example as were used in Example 3. In this Example, two passes were used instead of only a single pass. As before, the product from the first pass is used as the feed for the second pass, in which no ammonia is used. The product results are shown in Table II.

TABLE II

Product Analyses for Example 4

| Pass | Temp. °C. | Tallow Nitrile, lb/hr. | Cyclo-hexane, lb/hr. | $NH_3$, lb/hr. | Crude Product from 1st pass, lb/hr. | Product 1° amine, % | 2° amine, % | 3° amine, % |
|---|---|---|---|---|---|---|---|---|
| 1st | 155 | 0.28 | 0.57 | 0.06 | — | 50.6 | 48.6 | 0.9 |
| 2nd | 160 | — | 0.72 | 0 | 0.36 | 4.5 | 93.2 | 2.3 |

Again, much higher secondary amine yield was achieved by using two passes instead of one; compare 93.2% from Example 4 with the highest yield of 81.7% in Example 3.

Such excellent results in the continuous production of ditallowamine from tallow nitrile using a single catalyst are unknown in the art. Many modifications maybe made in the process of this invention without departing from the spirit and scope thereof which are defined only in the appended claims. For example, one skilled in the art may discover that particular reaction conditions or sequences, relative flow rates, or catalyst or promoter, which may not be explicitly recited herein, but which are nevertheless anticipated, would give desirable results.

I claim:

1. A continuous process for the preparation of secondary amines from fatty nitrile comprising continuously passing a nitrile over a nickel catalyst promoted with effective amounts of copper, chromium and molybdenum, where the process is carried out at a temperature in the range of about 130 to about 180° C. and a pressure in the range of about 50 to about 5000 psig, and where the nickel, copper, chromium and molybdenum are selected from the group consisting of nickel metal, nickel oxide, copper metal, copper oxide, chromium metal, chromium oxide, molybdenum metal and molybdenum oxide.

2. The process of claim 1 where the process is carried out in the presence of ammonia and hydrogen.

3. The process of claim 1 where the catalyst is at least 30% nickel oxide and at least 2% each of copper oxide, chromium oxide and molybdenum oxide.

4. The process of claim 1 where the nitrile has from 8 to 22 carbon atoms.

5. A continuous process for the preparation of secondary amines from nitriles comprising the steps of:
continuously passing a fatty nitrile over a nickle catalyst promoted with effective amounts of copper, chromium and molybdenum, in the presence of

TABLE I

Product Analyses for Example 5

| Temp. °C. | Feed Rate, Tallow Nitrile, lb/hr. | Feed Rate, Cyclohex-ane. lb/hr. | Feed Rate, $NH_3$, lb/hr. | Product Primary Amine. % | Secondary Amine, % | Tertiary Amine, % |
|---|---|---|---|---|---|---|
| 120 | 0.28 | 0.57 | 0.06 | 71.7 | 27.6 | 0.7 |
| 130 | 0.28 | 0.57 | 0.06 | 68.5 | 31.1 | 0.4 |
| 140 | 0.28 | 0.57 | 0.06 | 50.4 | 48.8 | 0.8 |
| 150 | 0.28 | 0.57 | 0.06 | 24.5 | 73.6 | 1.8 |
| 160 | 0.28 | 0.57 | 0.06 | 13.5 | 81.7 | 4.8 |
| 170 | 0.28 | 0.57 | 0.06 | 10.6 | 78.4 | 11.1 |
| 180 | 0.28 | 0.57 | 0.06 | 11.6 | 65.3 | 23.2 | added ammonia and hydrogen to produce an intermediate reaction product; and continuously passing the intermediate reaction product over the same catalyst in the presence of hydrogen but the absence of ammonia;

where the process is carried out at a temperature in the range of about 130 to about 180° C. and a pressure in the range of about 50 to about 5000 psig, and where the nickel, copper, chromium and molybdenum are selected from the group consisting of nickel metal, nickel oxide, copper metal, copper oxide, chromium metal, chromium oxide, molybdenum metal and molybdenum oxide.

6. The process of claim 5 where the catalyst is at least 30% nickel oxide and at least 2% each copper oxide, chromium oxide and molybdenum oxide.

7. The process of claim 5 where the nitrile has from 8 to 22 carbon atoms.

8. A continuous process for the preparation of secondary amines from nitriles comprising the steps of:

continuously passing a fatty nitrile having 8 to 22 carbon atoms over a nickel oxide catalyst promoted with effective amounts of copper oxide, chromium oxide and molybdenum oxide, in the presence of added ammonia and hydrogen to produce an intermediate reaction product; and where the catalyst is at least 30% nickel oxide and at least 2% each of copper oxide, chromium oxide and molybdenum oxide; and continuously passing the intermediate reaction product over the same catalyst in the presence of hydrogen but the absence of ammonia;

where the process is carried out at a temperature in the range of about 130 to about 180° C. and a pressure in the range of about 50 to about 5000 psig.

9. The process of claim 8 conducted in the absence of an additional catalyst.

* * * * *